(12) United States Patent
Kawamoto et al.

(10) Patent No.: US 11,903,684 B2
(45) Date of Patent: Feb. 20, 2024

(54) BLOOD PRESSURE MEASURING APPARATUS AND BLOOD PRESSURE MEASURING METHOD

(71) Applicants: HIROSHIMA UNIVERSITY, Higashihiroshima (JP); NIHON KOHDEN CORPORATION, Tokyo (JP)

(72) Inventors: Masashi Kawamoto, Hiroshima (JP); Noboru Saeki, Hiroshima (JP); Ryuji Nakamura, Hiroshima (JP); Teiji Ukawa, Tokyo (JP); Tsuneo Takayanagi, Tokyo (JP); Haruka Morimoto, Tokyo (JP)

(73) Assignees: HIROSHIMA UNIVERSITY, Hiroshima (JP); NIHON KOHDEN CORPORATION, Tokyo (JP)

( * ) Notice: Subject to any disclaimer, the term of this patent is extended or adjusted under 35 U.S.C. 154(b) by 0 days.

(21) Appl. No.: 14/625,820

(22) Filed: Feb. 19, 2015

(65) Prior Publication Data

US 2015/0245772 A1 Sep. 3, 2015

(30) Foreign Application Priority Data

Feb. 28, 2014 (JP) ................................. 2014-038510

(51) Int. Cl.
*A61B 5/022* (2006.01)
*A61B 5/021* (2006.01)
(Continued)

(52) U.S. Cl.
CPC ............ *A61B 5/022* (2013.01); *A61B 5/0205* (2013.01); *A61B 5/02108* (2013.01);
(Continued)

(58) Field of Classification Search
CPC ... A61B 5/0205; A61B 5/02108; A61B 5/022; A61B 5/0816
See application file for complete search history.

(56) References Cited

U.S. PATENT DOCUMENTS

| 5,094,244 A | 3/1992 | Callahan et al. |
| 2004/0044290 A1* | 3/2004 | Ward ..................... A61B 5/022 600/490 |

(Continued)

FOREIGN PATENT DOCUMENTS

| JP | 2011-511686 A | 4/2011 |
| JP | 2012-205822 A | 10/2012 |

OTHER PUBLICATIONS

Cannesson et al, Respiratory Variations in Pulse Oximetry Plethysmographic Waveform Amplitude to Predict Fluid Responsiveness in the Operating Room, 2007, Anesthesiology, 106(6): 1105-11.*

(Continued)

*Primary Examiner* — Tse W Chen
*Assistant Examiner* — Michael A Catina
(74) *Attorney, Agent, or Firm* — Sughrue Mion, PLLC (57) ABSTRACT

A blood pressure measuring apparatus includes a pressure control unit that controls an applied pressure applied to a region of a living body in which a vein and artery exist by a cuff mountable to the region, a detection unit that detects pressure waveforms in which pulse wave components from the region overlap with the applied pressure, and an analysis unit that obtains a respiratory variation on the waveform of artery and a venous pressure based on the pressure waveforms detected by the detection unit through one-time blood pressure measurement. The analysis unit obtains the respiratory variation on the waveform of artery based on data of a first pressure waveform in a first process, and the venous pressure based on data of a second pressure waveform in a second process and the data of the first pressure waveform.

12 Claims, 7 Drawing Sheets

(51) Int. Cl.
*A61B 5/00* (2006.01)
*A61B 5/0205* (2006.01)
*A61B 5/08* (2006.01)

(52) U.S. Cl.
CPC ........ *A61B 5/02225* (2013.01); *A61B 5/0816* (2013.01); *A61B 5/7203* (2013.01); *A61B 5/7221* (2013.01); *A61B 5/7278* (2013.01); *A61B 5/742* (2013.01)

(56) References Cited

U.S. PATENT DOCUMENTS

| | | | | |
|---|---|---|---|---|
| 2004/0059234 | A1* | 3/2004 | Martin | A61B 5/022 600/500 |
| 2006/0247540 | A1* | 11/2006 | Ide | A61B 5/022 600/490 |
| 2010/0292592 | A1* | 11/2010 | Parfenov | A61B 5/02116 600/507 |
| 2010/0324428 | A1 | 12/2010 | Pfeiffer | |
| 2011/0201961 | A1* | 8/2011 | Hu | A61B 5/02028 600/561 |
| 2012/0253209 | A1 | 10/2012 | Ukawa et al. | |
| 2014/0343600 | A1* | 11/2014 | Leschinsky | A61B 5/0225 606/202 |

OTHER PUBLICATIONS

Ward, et al.; "A New Noninvasive Method to Determine Central Venous Pressure", Resuscitation, Elsevier, vol. 70, No. 2, Aug. 2006, 9 pages total.

Ward, et al.; "A Novel Noninvasive Impedance Based Technique for Central Venous Pressure Measurement", Shock, vol. 33, No. 1, Mar. 2010, 9 pages total.

Search Report dated Aug. 4, 2015, issued by the European Patent Office in counterpart European Application No. 15155742.8.

\* cited by examiner

BLOOD PRESSURE MEASURING APPARATUS AND BLOOD PRESSURE MEASURING METHOD

CROSS REFERENCE TO RELATED APPLICATION

This application is based on Japanese Patent Applications No. 2014-038510 filed on Feb. 28, 2014, the contents of which are incorporated herein by reference.

BACKGROUND

The presently disclosed subject matter relates to a blood pressure measuring apparatus and a blood pressure measuring method for measuring a blood pressure by using an oscillometric method.

When assessing hemodynamics, a respiratory variation on the waveform of artery and a central venous pressure are important indexes. In the related art, in order to obtain the central venous pressure, for example, a catheter inserted to measure a correct central venous pressure. However, since the measuring method is invasive, an excessive burden may be applied to a subject being tested. Also, a measuring apparatus is enlarged and a measurement time is prolonged. For this reason, a method for measuring the central venous pressure by a non-invasive and simple method has been suggested.

For example, JP-A-2012-205822 discloses measuring an mean venous pressure by using an oscillometric principle. Also, JP-A-2011-511686 discloses measuring an arterial pressure and a pulse pressure variation to respiratory variation on the waveform of artery) within a respiratory period by an oscillometric blood pressure measurement.

However, since the mean venous pressure measured by the method disclosed in JP-A-2012-205822 and the respiratory variation on the waveform of artery measured by the method disclosed in JP-A-2011-511686 are respectively measured by the separate methods, it is thought that a relativity therebetween is not necessarily high. For this reason, it is thought that the hemodynamics assessed based on the measured parameters does not necessarily have the sufficient reliability. Also, since the respective parameters are separately measured, it takes time to measure the parameters and a rapid diagnosis may be disturbed.

It is therefore an object of the presently disclosed subject matter to provide a blood pressure measuring apparatus and a blood pressure measuring method capable of simply and correctly assessing hemodynamics of a living body.

SUMMARY (1) A blood pressure measuring apparatus includes a pressure control unit that controls an applied pressure applied to a region of a living body in which a vein and artery exist by a cuff mountable to the region, a detection unit that detects pressure waveforms in which pulse wave components from the region overlap with the applied pressure, and an analysis unit that obtains a respiratory variation on the waveform of artery and a venous pressure based on the pressure waveforms detected by the detection unit through one-time blood pressure measurement. The analysis unit obtains the respiratory variation on the waveform of artery based on data of a first pressure waveform of the pressure waveforms in a first process, in which the applied pressure is kept at a constant pressure by the pressure control unit, and the venous pressure based on data of a second pressure waveform of the pressure waveforms in a second process in which the applied pressure is decreased or increased by the pressure control unit, and the data of the first pressure waveform in the first process.

According to the configuration (1), it is possible to obtain the parameters of the respiratory variation on the waveform of artery and the venous pressure at once based on the applied pressure and the pulse wave components overlapping with the applied pressure in one-time blood pressure measurement. For this reason, it is possible to obtain the respective parameters in a non-invasive and simple manner in a series of measuring processes. Also, since the two parameters are obtained based on the applied pressure and the pulse wave components obtained in one-time blood pressure measurement, it is possible to obtain the parameters having higher relativity, as compared to a configuration where the parameters are obtained based on the applied pressure and the pulse wave components obtained by measurement of a separate measuring process or by mounting the cuff to a separate region. Therefore, it is possible to correctly assess the hemodynamics based on the parameters having high relativity. Also, since the respiratory variation on the waveform of artery is obtained during a time period for which the applied pressure is controlled at a constant pressure, it is possible to correctly obtain variation components based on the respiration, which are included in the pressure waveform. Also, since the venous pressure is obtained during a time period for which the applied pressure is decreased or increased, it is possible to gradually change (decrease or increase) the pulse wave components of the arterial pressure included in the pressure waveform, thereby correctly obtaining the venous pressure.

(2) In the blood pressure measuring apparatus of (1), the applied pressure in the first process is equal to or lower than a diastolic blood pressure and within a range which does not include a pulse wave component of the vein in the pulse wave components.

According to the configuration (2), since the applied pressure is kept at a pressure equal to or lower than the diastolic blood pressure and not including the pulse wave components of the vein, it is possible to obtain the respiratory variation on the waveform of artery more correctly.

(3) In the blood pressure measuring apparatus of (1) or (2), the analysis unit is configured to obtain the venous pressure based on the data of the pressure waveform in the second process when correlativity between the data of the pressure waveform in the second process and the data of the pressure waveform in the first process is low.

According to the configuration (3), since the venous pressure is obtained based on the data of the pressure waveform in the second process having low correlativity with respect to the data of the pressure waveform in the first process, it is possible to suppress an influence of the arterial pressure, thereby obtaining the venous pressure more correctly.

(4) In the blood pressure measuring apparatus of (1) or (2), the analysis unit is configured to obtain an arterial pressure by one-time blood pressure measurement and based on data of a third pressure waveform of the pressure waveforms in a third process, in which the applied pressure is increased or decreased by the pressure control unit.

According to the configuration (4), it is possible to obtain the three parameters of the arterial pressure, the respiratory variation on the waveform of artery and the venous pressure at once in one-time blood pressure measurement. For this reason, it is possible to obtain the respective parameters in a non-invasive and simple manner in a series of measuring processes. Also, when obtaining the arterial pressure during a time period for which the applied pressure is increased, it is possible to complete the measurement of the arterial pressure in a short time. Therefore, since it is possible to secure the longer time necessary for obtaining the respiratory variation on the waveform of artery and the venous pressure in the series of measuring processes, it is possible to obtain the three parameters securely and correctly.

(5) In the blood pressure measuring apparatus of (4), the analysis unit is configured to obtain the venous pressure based on the data of the second pressure waveform in the second process and the data of the third pressure waveform in the third process or the data of the first pressure waveform in the first process.

According to the configuration (5), since the venous pressure is obtained based on any one of the data of the pressure waveform in the first process and the data of the pressure waveform in the third process, a choice of calculation is increased. Thereby, it is possible to sufficiently check the relativity with the pulse wave components of the arterial pressure, thereby obtaining the venous pressure more correctly.

(6) In the blood pressure measuring apparatus of (5), the analysis unit is configured to obtain the venous pressure based on the data of the second pressure waveform in the second process when a correlativity between the data of the second pressure waveform in the second process and the data of the third pressure waveform in the third process or the data of the first pressure waveform in the first process is low.

According to the configuration (6), since the venous pressure is obtained based on the data of the pressure waveform in the second process having low correlativity with respect to one of the data of the waveforms in the first and third processes, it is possible to suppress the influence of the arterial pressure, thereby obtaining the venous pressure more correctly.

(7) In the blood pressure measuring apparatus of any one of (1) to (6), the blood pressure measuring apparatus further includes a display unit, and a display control unit that controls the display unit. The display control unit is configured to display a value of the obtained respiratory variation on the waveform of artery and a value of the obtained venous pressure with a two-dimensional graph on the display unit.

According to the configuration (7), since a relativity between the obtained value of the respiratory variation on the waveform of artery and the obtained value of the venous pressure is displayed as the two-dimensional graph on the display unit, a medical staff who is monitoring the biological information can comprehensively determine the two parameters of the respiratory variation on the waveform of artery and the venous pressure by seeing the display unit, thereby correctly assessing the hemodynamics.

(8) In the blood pressure measuring apparatus of (7), a determination criterion for determining the displayed value of the respiratory variation on the waveform of artery and the displayed value of the venous pressure is displayed on the two-dimensional graph.

According to the configuration (8), since it is possible to determine the respiratory variation on the waveform of artery and the venous pressure based on the determination criterion displayed on the two-dimensional graph, the medical staff who is monitoring the biological information can easily assess the hemodynamics.

(9) A blood pressure measuring method for controlling an applied pressure applied to a region of a living body in which a vein and an artery exist by a cuff mountable to the region, detecting pressure waveforms in which pulse wave components are overlapped with the applied pressure, and obtaining a on the waveform of artery of an arterial pressure and a venous pressure based on the detected pressure waveforms, includes obtaining the respiratory variation on the waveform of artery based on data of a first pressure waveform of the pressure waveforms in a first process, in which the applied pressure is kept at a constant pressure, and obtaining the venous pressure based on data of a second pressure waveform of the pressure waveforms in a second process, in which the applied pressure is decreased or increased, and the data of the first pressure waveform. The first process and the second process are performed by one-time blood pressure measurement.

According to the configuration (9), it is possible to obtain the parameters of the respiratory variation on the waveform of artery and the venous pressure at once based on the applied pressure and the pulse wave components overlapping with the applied pressure in one-time blood pressure measurement. For this reason, it is possible to obtain the respective parameters in a non-invasive and simple manner in a series of measuring processes. Also, since the two parameters are obtained based on the applied pressure and the pulse wave components obtained in one-time blood pressure measurement, it is possible to obtain the parameters having higher relativity, as compared to a configuration where the parameters are obtained based on the applied pressure and the pulse wave components obtained by measurement of a separate measuring process or by mounting the cuff to a separate region. Therefore, it is possible to correctly assess the hemodynamics based on the parameters having high relativity. Also, since the respiratory variation on the waveform of artery is obtained during a time period for which the applied pressure is controlled at a constant pressure, it is possible to correctly obtain variation components based on the respiration, which are included in the pressure waveform. Also, since the venous pressure is obtained during a time period for which the applied pressure is decreased or increased, it is possible to gradually change (decrease or increase) the pulse wave components of the arterial pressure included in the pressure waveform, thereby correctly obtaining the venous pressure.

According to the blood pressure measuring apparatus of the presently disclosed subject matter, it is possible to assess the hemodynamics of the living body simply and correctly.

DETAILED DESCRIPTION OF EMBODIMENTS

Hereinafter, an illustrative embodiment of a blood pressure measuring apparatus of the presently disclosed subject matter will be described in detail with reference to the drawings.

Figure 1:
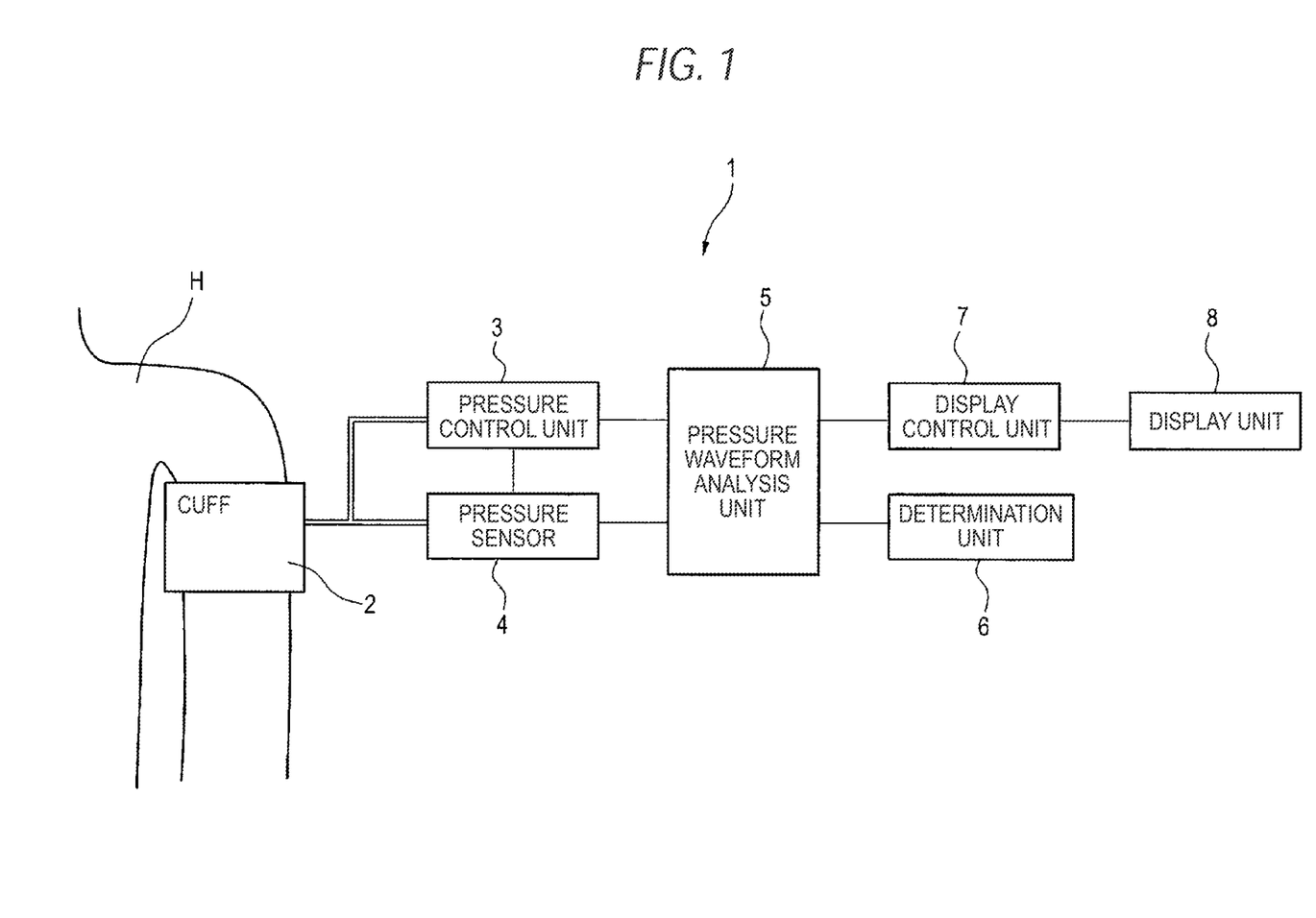
FIG. 1 is a functional block diagram showing a configuration of a blood pressure measuring apparatus according to an illustrative embodiment of the presently disclosed subject matter.

FIG. 1 is a functional block diagram showing a configuration of a blood pressure measuring apparatus 1 according to an illustrative embodiment of the presently disclosed subject matter.

As shown in FIG. 1, the blood pressure measuring apparatus 1 has a cuff 2, a pressure control unit 3, a pressure sensor (an example of a detection unit) 4, a pressure waveform analysis unit (an example of an analysis unit) 5, a determination unit 6, a display control unit 7 and a display unit 8.

The cuff 2 is wound and mounted to a part of a living body at which the vein and artery of a subject being tested (an example of a living body) can be detected, for example, to a brachial region (an example of a region) in the vicinity of an axillary region. The cuff 2 has a pressure pouch (not shown), and a cuff pressure (an example of an applied pressure) is applied from the cuff 2 to the brachial region by an air pressure of the pressure pouch.

The pressure control unit 3 is configured to control the air pressure of the pressure pouch of the cuff 2. The air pressure of the pressure pouch is controlled by a pressurization pump, an electromagnetic valve, a control circuit and the like included in the pressure control unit 3. All of them are not shown in the drawings.

The pressure sensor 4 is configured to detect a pressure waveform in which pulse wave components overlap with the cuff pressure. When the cuff pressure is applied to the brachial region, a pulse wave, which is a vibration of a blood vessel wall, overlaps with the cuff pressure in synchronization with the pulse of the subject being tested H. The pressure sensor 4 is configured to detect the pressure waveform in which the pulse wave components from the brachial region overlap, and to transmit the detected pressure waveform to the pressure waveform analysis unit 5.

The pressure waveform analysis unit 5 is configured to obtain a diastolic blood pressure, an mean blood pressure and a systolic blood pressure (an example of an arterial pressure), a respiratory variation on the waveform of artery, and an mean venous pressure (an example of a venous pressure) measured at the vein of the brachial region in the vicinity of the axillary region, based on the cuff pressures and pulse wave components included in the pressure waveform. The pressure waveform analysis unit 5 is configured to obtain the respiratory variation on the waveform of artery and the mean venous pressure together with the blood pressure in one-time measuring process of measuring the blood pressure. In the meantime, it is said that the mean venous pressure measured at the vein of the brachial region is substantially equivalent to a central venous pressure measured by an invasive method.

The determination unit 6 is configured to determine the reliability of the respiratory variation on the waveform of artery and mean venous pressure obtained by the pressure waveform analysis unit 5. The determination unit is configured to determine the reliability by taking correlations between a representative pulse wave and the pulse waves overlapping with the respective cuff pressures during a time period for which the respiratory variation on the waveform of artery is obtained and during a time period for which the mean venous pressure is obtained.

The display control unit 7 is configured to display on the display unit 8 the information of the diastolic blood pressure, the systolic blood pressure, the mean blood pressure, the respiratory variation on the waveform of artery, the mean venous pressure and the like. The display unit 8 is configured by a touch panel-type liquid crystal screen, for example.

Subsequently, operations of the blood pressure measuring apparatus 1 are described based on a flowchart shown in FIG. 2, with reference to FIGS. 3 to 6. In below descriptions, the measurement of the pulse wave component and the determination of the arterial pressure, the respiratory variation on the waveform of artery and the mean venous pressure are made substantially at the same time. However, only the measurement of the cuff pressure and the pulse wave component may be first made and the determination of the arterial pressure, the respiratory variation on the waveform of artery and the mean venous pressure may be separately made using the data of the measured cuff pressure and the like.

Figure 2:
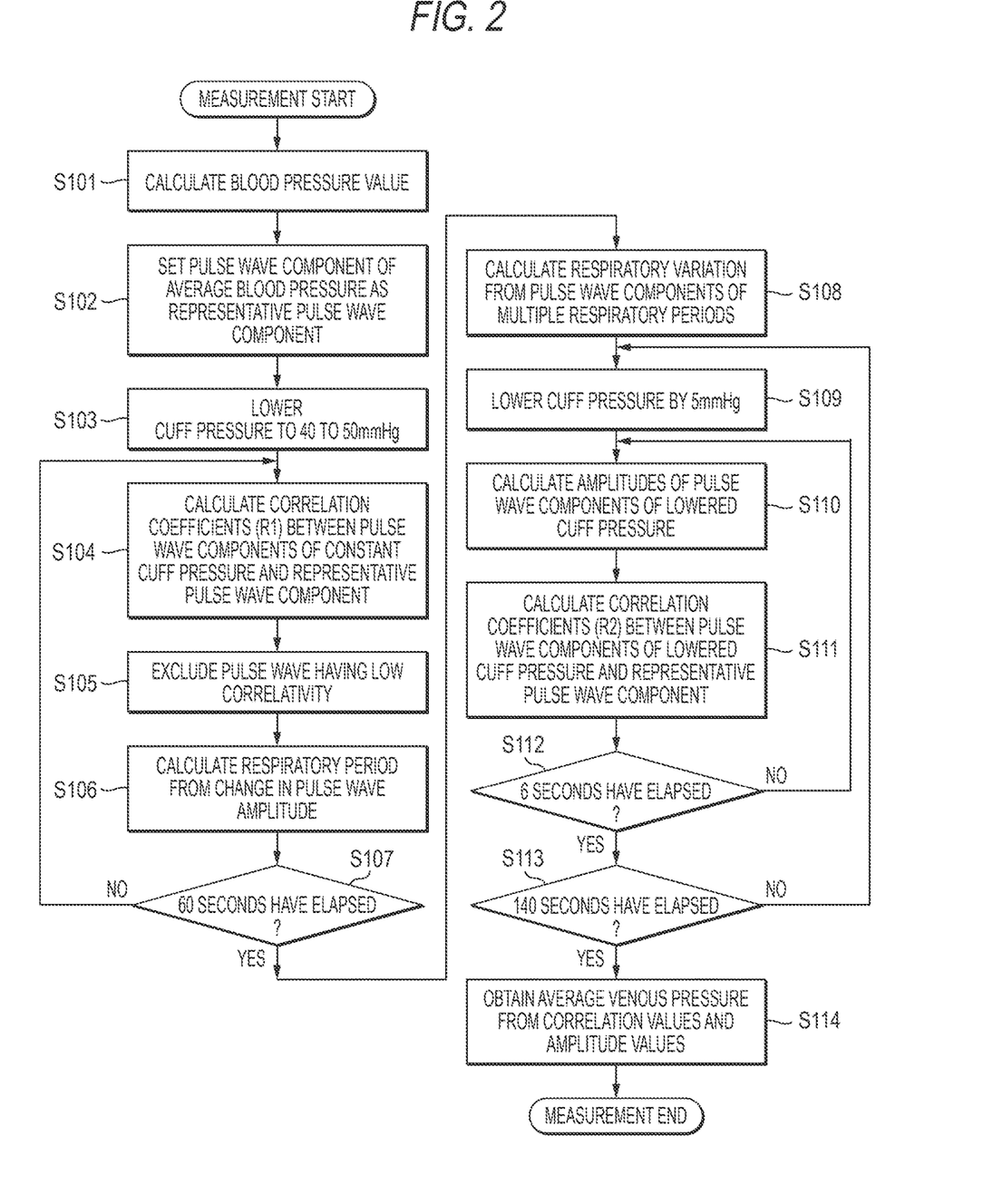
FIG. 2 is a flowchart for illustrating operations of the blood pressure measuring apparatus.

As shown in FIG. 2, when the measurement of the blood pressure measuring apparatus 1 starts, a blood pressure value is first measured (step S101). The blood pressure value is non-invasively measured by the oscillometric method. The cuff pressure of the cuff 2 wound on the brachial region is gradually or stepwise increased by the pressure control unit 3. A pressure waveform in the pressurization process (a third process) is detected by the pressure sensor 4, and the cuff pressures and pulse wave components (an example of data of the pressure waveform) included in the pressure waveform are measured and analyzed by the pressure waveform analysis unit 5. The pressure waveform analysis unit 5 obtains the diastolic blood pressure, the mean blood pressure and the systolic blood pressure based on a change in the pulse wave component.

Specifically, when the cuff pressure is increased, an amplitude of the pulse wave component overlapping with the cuff pressure is correspondingly increased. When the cuff pressure becomes the same as a blood pressure applied to the blood vessel wall, the amplitude of the pulse wave component becomes largest. When the cuff pressure is further increased, the amplitude of the pulse wave component decreases. The pressure waveform analysis unit 5 determines, as the mean blood pressure, the cuff pressure at the time that the amplitude of the pulse wave component becomes largest. Also, the pressure waveform analysis unit 5 obtains a pulse wave amplitude at the diastolic blood pressure and a pulse wave amplitude at the systolic blood pressure by a predetermined calculation equation, based on the maximum amplitude of the pulse wave component. At this time, the diastolic blood pressure is a cuff pressure lower than the mean blood pressure and is a cuff pressure at the time that the pulse wave amplitude being measured coincides with the pulse wave amplitude at the diastolic blood pressure obtained by the calculation equation. Also, the systolic blood pressure is a cuff pressure higher than the mean blood pressure and is a cuff pressure at the time that the pulse wave amplitude being measured coincides with the pulse wave amplitude at the systolic blood pressure obtained by the calculation equation. In the meantime, it may be possible to measure the mean blood pressure, the systolic blood pressure and the diastolic blood pressure while the cuff pressure is rapidly increased to a pressure higher than the systolic blood pressure and is then gradually reduced.

Figure 3A:
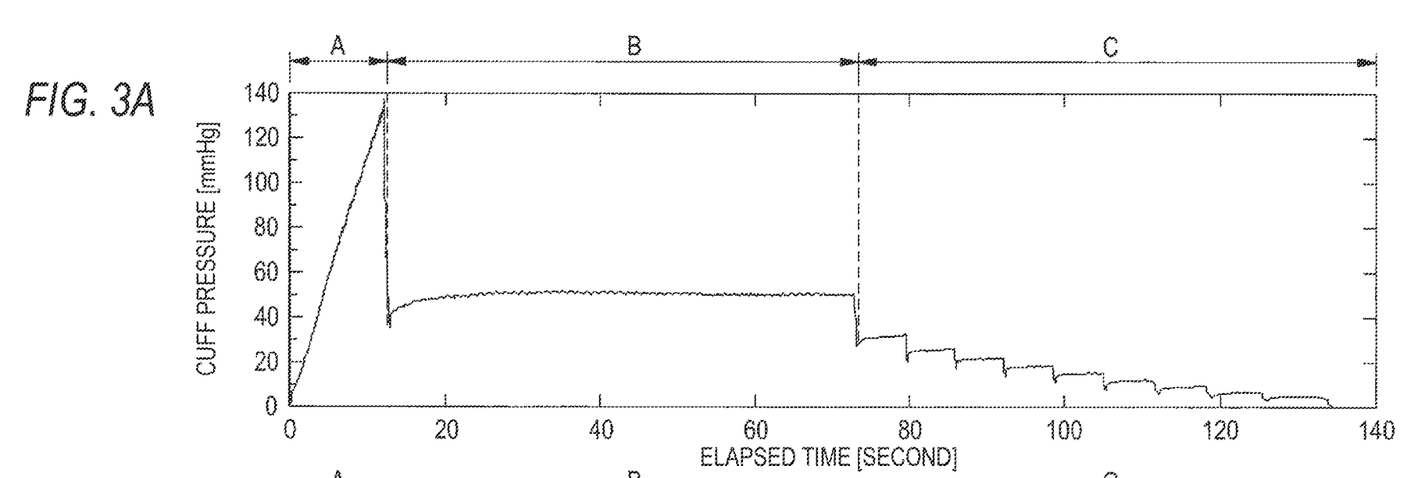
FIG. 3A illustrates a change in a cuff pressure during measurement of the blood measuring apparatus.
Figure 3B:
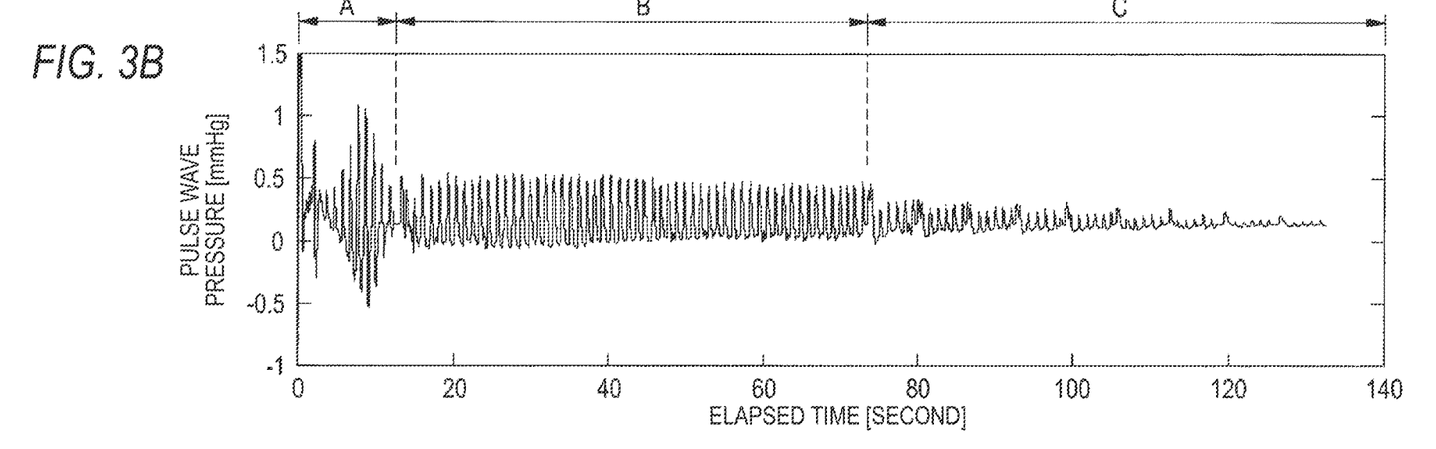
FIG. 3B illustrates pulse wave components overlapping with the cuff pressure of FIG. 3A.

FIG. 3 illustrates a change in the pressure detected during one-time measurement of the blood pressure measurement apparatus 1. FIG. 3A illustrates a change in the pressure waveform (in which the pulse wave components overlap with the cuff pressures) over elapsed measurement time of the blood pressure measuring apparatus 1. Also, FIG. 3B illustrates the pulse wave components in the pressure waveform of FIG. 3A.

The diastolic blood pressure, the mean blood pressure and the systolic blood pressure are measured during the pressurization process of the cuff pressure, which is a time period A shown in FIG. 3A. The measurement of the above blood pressures is completed at the time that the systolic blood pressure is measured. The blood pressure measurement during the time period A is completed at about 15 seconds after the measurement starts.

Subsequently, the pressure waveform analysis unit 5 extracts the pulse wave component in the mean blood pressure of the blood pressures obtained in step S101, as a representative pulse wave component (step S102).

Figure 4:
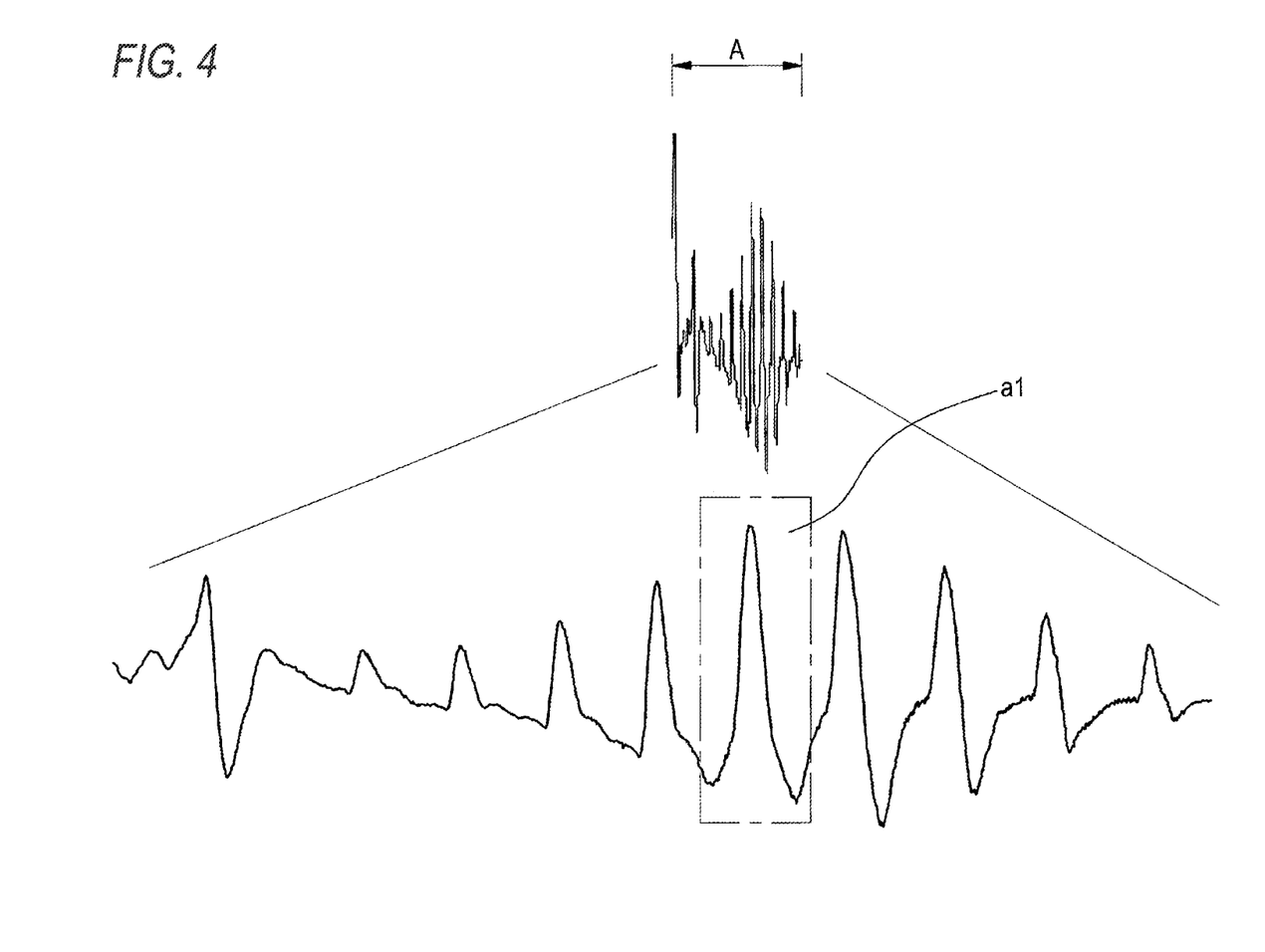
FIG. 4 illustrates the overlapping pulse wave components during an arterial pressure measurement time period.

FIG. 4 illustrates the pulse wave components during the time period A in FIG. 3. The pulse wave component having the largest amplitude of the pulse wave components during the time period A is extracted as a representative pulse wave component a1, which is the pulse wave component of the mean blood pressure.

Subsequently, in order to obtain the respiratory variation on the waveform of artery, the cuff pressure is reduced to a pressure within a range equal to or lower than the diastolic blood pressure and not including the pulse wave component of the vein, for example, 40 to 50 mmHg (step S103). By reducing the cuff pressure to the pressure within the range, when obtaining the respiratory variation on the waveform of artery, the artery is not excessively occluded and the pulse of the vein does not influence.

The respiratory variation on the waveform of artery is obtained during a constant pressure (for example, about 50 mmHg) process (a first process) of the cuff pressure, which is a time period B shown in FIG. 3A. During the time period B, the multiple respiratory variations on the waveform of artery are obtained. For this reason, the cuff pressure is kept at a constant pressure equal to or lower than the diastolic blood pressure continuously for a predetermined time period (for example, 60 seconds). In the meantime, the pressure that is kept constant is not limited to the pressure equal to or lower than the diastolic blood pressure inasmuch as an influence of the pulse of the venous pressure does not appear in the pressure. For example, a pressure near the diastolic blood pressure may also be used.

Subsequently, the determination unit 6 calculates correlation coefficients R1 between the pulse wave components overlapping with the cuff pressure kept at a constant pressure and the representative pulse wave component a1 extracted in step S102 (step S104).

Figure 5:
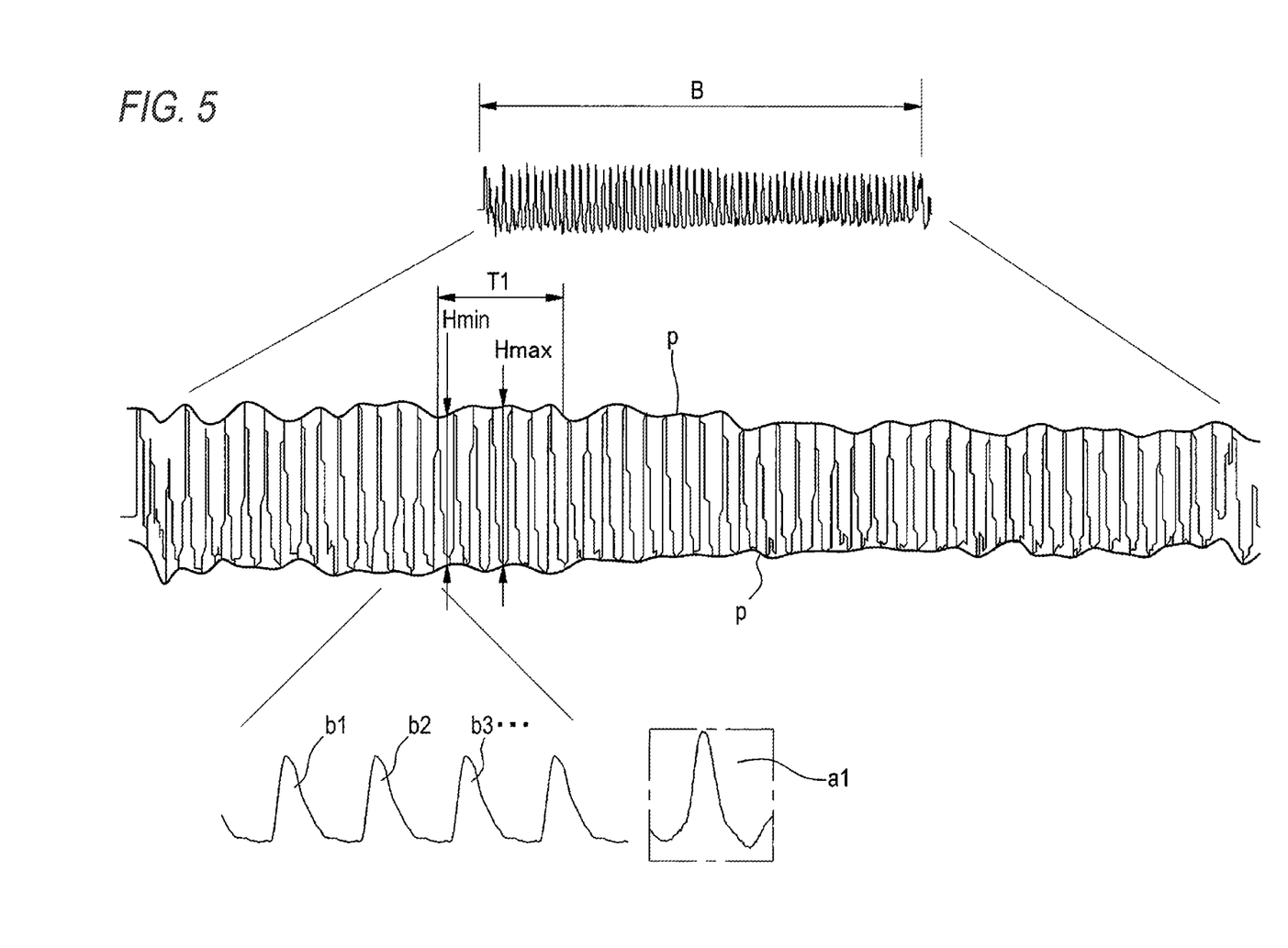
FIG. 5 illustrates the overlapping pulse wave components during a respiratory variation measurement time period.

FIG. 5 illustrates the extracted pulse wave components during the time period B of FIG. 3. During the time period B, individual pulse wave components b1, b2, b3, . . . are extracted by the pressure waveform analysis unit 5. The correlation coefficients R1 between the extracted individual pulse wave components b1, b2, b3, . . . and the representative pulse wave component a1 are calculated.

Subsequently, the determination unit 6 extracts the pulse wave component having low correlativity based on the correlation coefficients R1, and excludes the extracted pulse wave component so that it is not used as a pulse wave component for obtaining the respiratory variation on the waveform of artery (step S105). In order to obtain the respiratory variation on the waveform of artery having the higher reliability, it is preferable that the pulse wave component of the vein does not influence the pulse wave components b1, b2, b3, . . . during the time period B. The pulse wave components b1, b2, b3, . . . , which are not influenced by the pulse wave component of the vein, have the high correlativity with the representative pulse wave component a1, which is a typical pulse wave of the artery. For this reason, the pulse wave component having the low correlativity is excluded and the pulse wave component having the high correlativity is used as the pulse wave component for obtaining the respiratory variation on the waveform of artery. Thereby, it is possible to improve the reliability of the obtained respiratory variation on the waveform of artery.

Subsequently, the pressure waveform analysis unit 5 calculates amplitudes of the extracted pulse wave components b1, b2, b3, . . . , and calculates a respiratory period of the subject being tested H from a change in the amplitude (step S106). Then, it is determined whether 60 seconds have elapsed after the measurement of the respiratory variation on the waveform of artery has started (step S107). When 60 seconds have not elapsed, each step from step S104 is repeated. On the other hand, when 60 seconds have elapsed, the pressure waveform analysis unit 5 obtains the respiratory variation on the waveform of artery of the subject being tested H based on the amplitude variation of the pulse wave components during the plurality of calculated respiratory periods (step S108).

Solid lines p shown in FIG. 5 indicate envelope curves connecting peaks of the pulse wave components, and a time period T1 indicates the respiratory period. Also, an amplitude Hmax indicates a maximum amplitude of the pulse wave component, and an amplitude Hmin indicates a minimum amplitude of the pulse wave component. The respiratory variation on the waveform of artery is calculated by an equation of $((Hmax-Hmin)/((Hmax+Hmin)/2))*100[\%]$. By the calculation equation, the respiratory variation on the waveform of artery is calculated during the multiple respiratory periods.

As shown in FIG. 3A, the measurement of the respiratory variation on the waveform of artery is completed at about 75 seconds after the measurement starts.

Subsequently, in order to obtain the mean venous pressure, the pressure control unit 3 stepwise (for example, by 5 mmHg) lowers the cuff pressure (step S109).

The mean venous pressure is obtained in a depressurization process of the cuff pressure (a second process), which is a time period C shown in FIG. 3A. The mean venous pressure is measured continuously to the measurement of the respiratory variation on the waveform of artery, and the cuff pressure is stepwise reduced over time from the constant pressure (for example, about 50 mmHg) at which the respiratory variation on the waveform of artery is measured.

Subsequently, the pressure waveform analysis unit 5 calculates the amplitudes of the pulse wave components overlapping with the cuff pressure reduced by 5 mmHg (step S110). Then, the determination unit 6 calculates correlation coefficients R2 between the pulse wave components overlapping with the cuff pressure reduced by 5 mmHg and the representative pulse wave component a1 extracted in step S102 (step S111).

Figure 6:
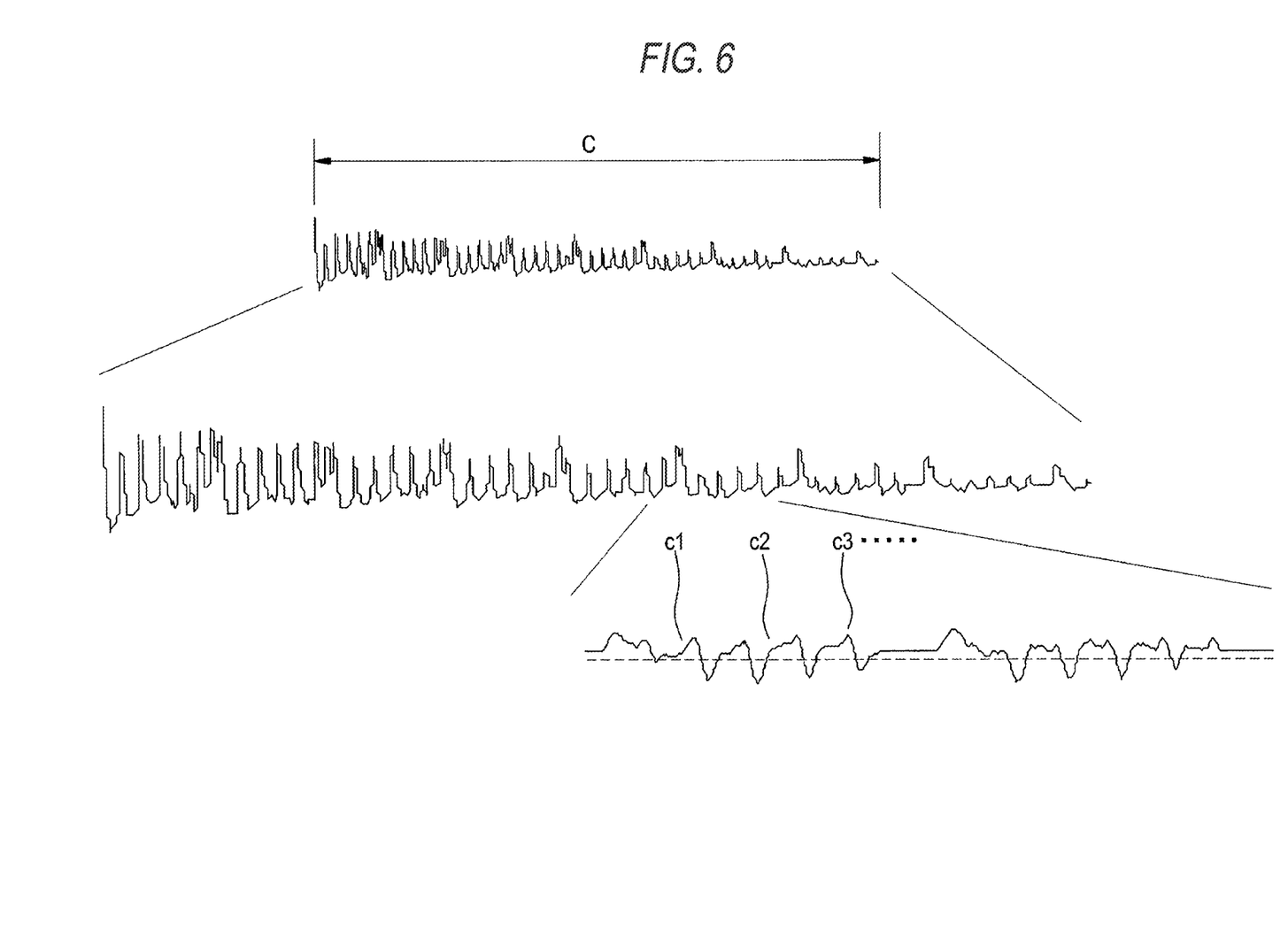
FIG. 6 illustrates the overlapping pulse wave components during a venous pressure measurement time period.

FIG. 6 illustrates the extracted pulse wave components during the time period C of FIG. 3. During the time period C, individual pulse wave components c1, c2, c3, . . . are extracted and amplitudes thereof are calculated. The correlation coefficients R2 between the extracted individual pulse wave components c1, c2, and the representative pulse wave component a1 are calculated.

Subsequently, it is determined whether 6 seconds have elapsed after the cuff pressure is reduced by 5 mmHg (step S112). When 6 seconds have not elapsed, each step from step S110 is repeated. On the other hand, when 6 seconds have elapsed, it is determined whether 140 seconds have elapsed after the measurement of the blood pressure has started (step S113). When 140 seconds have not elapsed, the processing is returned to step S109, the cuff pressure is further reduced by 5 mmHg and each step from step S110 is then repeated. On the other hand, when 140 seconds have elapsed, the pressure waveform analysis unit 5 obtains the mean venous pressure based on the amplitudes of the pulse wave components calculated in step S110 and the correlation coefficients R2 calculated in step S111 (step S114).

Specifically, when the cuff pressure stepwise reduced, the pulse wave components of the artery overlapping with the cuff pressure are correspondingly reduced and the pulse wave components of the vein are gradually increased. For this reason, the correlation coefficient R2 with the representative pulse wave component a1, which is the typical pulse of the artery, is gradually decreased. When the cuff pressure is further reduced, the pulse wave components of the vein are further increased. When the cuff pressure becomes equal to the blood pressure applied to the blood vessel wall, the amplitudes of the pulse wave components of the vein show peaks. Based on this, the mean venous pressure is obtained by the pulse wave components of the second process and the correlativity between the pulse wave components of the second process and the pulse wave components of the first process. In the meantime, since the pulse wave components of the vein are smaller, as compared to the pulse wave components of the artery, even though the cuff pressure is reduced and the pulse wave components of the artery are thus decreased, the pulse wave components of the artery may influence the observation of the pulse wave components of the vein. In this case, it may not possible to clearly detect the peaks of the amplitudes of the pulse wave components of the vein. For this reason, the pressure waveform analysis unit 5 performs the overall analysis on condition that the correlativity is low and the amplitude of the pulse wave component shows a peak, and determines the cuff pressure at that time, as the mean venous pressure. Then, the pressure waveform analysis unit estimates the determined mean venous pressure as a central venous pressure.

In this way, the measurement of each parameter is completed.

Subsequently, data that is displayed on the display unit 8 of the blood pressure measuring apparatus 1 is described with reference to FIG. 7.

Figure 7:
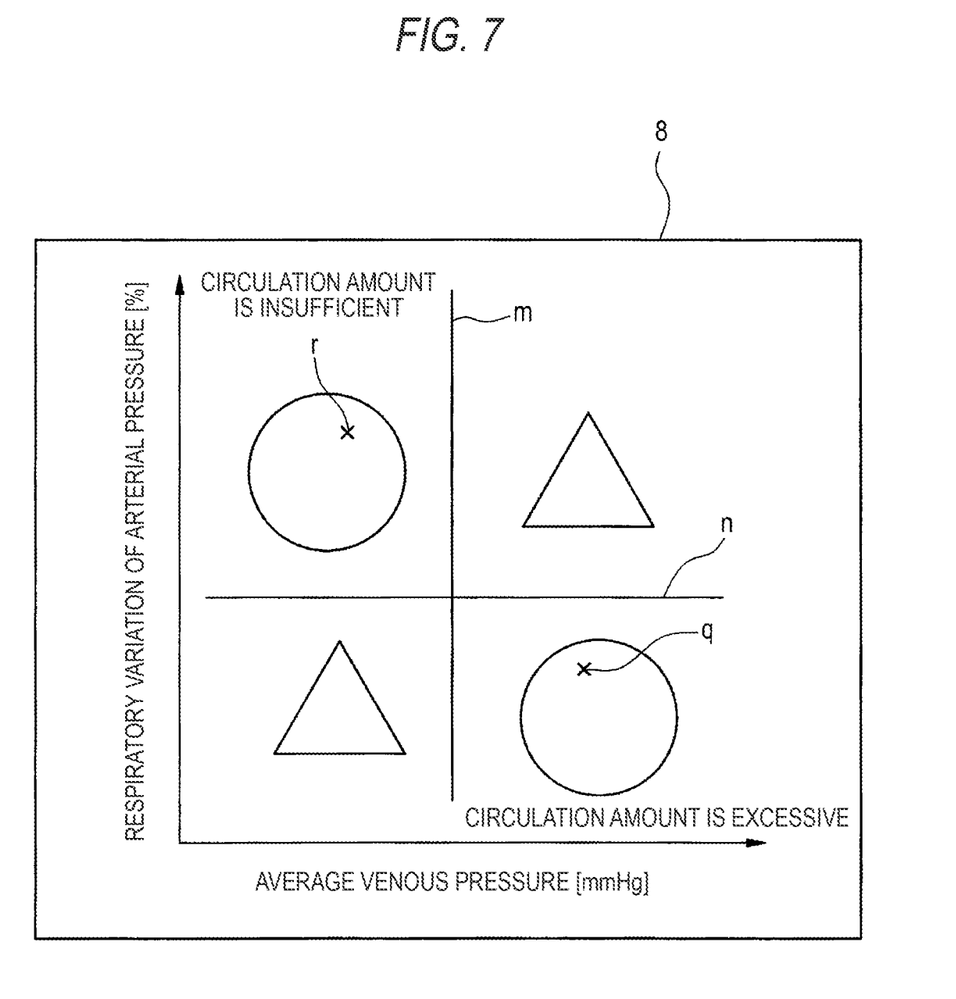
FIG. 7 is a graph showing a relativity between the respiratory variation and the venous pressure.

As shown in FIG. 7, the values of the respiratory variation on the waveform of artery and the values of the mean venous pressure obtained as described above are displayed as a two-dimensional graph on the display unit 8. Also, a determination criterion for determining the value of the respiratory variation on the waveform of artery and the value of the mean venous pressure is displayed as threshold lines m, n, for example.

Based on the display of the two-dimensional graph, the hemodynamics of the subject being tested is determined as follows. For example, when the obtained value of the respiratory variation on the waveform of artery and the obtained value of the mean venous pressure are a point q on the graph, the value of the respiratory variation on the waveform of artery is below the threshold line n and the value of the mean venous pressure is above the threshold line m, it is determined that circulating blood volume is excessive. Also, for example, when the obtained values are a point r, the value of the respiratory variation on the waveform of artery is above the threshold line n and the value of the mean venous pressure is below the threshold line m, it is determined that circulating blood volume is insufficient.

Also, although not shown in FIG. 7, the values of the diastolic blood pressure, systolic blood pressure and mean blood pressure obtained as described above are also displayed simultaneously with the display of the two-dimensional graph on the display unit 8.

According to the blood pressure measuring apparatus of the illustrative embodiment, during one-time blood pressure measurement by the oscillometric method, the parameters of the diastolic blood pressure, mean blood pressure, systolic blood pressure, respiratory variation on the waveform of artery and mean venous pressure can be obtained at once based on the cuff pressure applied from the cuff 2 to the brachial region and the pulse wave components overlapping with the cuff pressure. For this reason, it is possible to obtain the respective parameters in a non-invasive and simple manner in a series of measuring processes. Also, since all the parameters are obtained based on the cuff pressure and the pulse wave components overlapping with the cuff pressure obtained in one-time blood pressure measurement, the relativity of the parameters is very high, as compared to a configuration where the parameters are obtained based on the cuff pressure and the pulse wave components overlapping with the cuff pressure obtained by measurement of a separate measuring process or by mounting the cuff 2 to a separate region. That is, while the respiratory variation on the waveform of artery and the mean venous pressure obtained by the method of the related art are the indexes having low reliability, it is possible to correctly assess the hemodynamics of the subject being tested H based on the parameters having high relativity, in accordance with the illustrative embodiment of the presently disclosed subject matter.

Also, since the diastolic blood pressure, mean blood pressure, systolic blood pressure are measured during the pressurization process of the cuff pressure, it is possible to shorten the time necessary to complete the measurement of the above blood pressures, as compared to a configuration where the cuff pressure is increased above the systolic blood pressure and the diastolic blood pressure, mean blood pressure, systolic blood pressure are measured during the depressurization process of the cuff pressure. Thereby, since it is possible to secure the longer time necessary for obtaining the respiratory variation on the waveform of artery and the mean venous pressure in the series of measuring processes, it is possible to obtain the parameters securely and correctly.

Also, since the respiratory variation on the waveform of artery is obtained during the time period for which the cuff pressure is kept at a constant pressure, it is possible to clearly plot the envelope curves p connecting the peaks of the pulse wave components, so that it is possible to correctly obtain the variation components based on the respiration of the subject being tested, which are included in the pressure waveform. Also, since about 60 seconds are secured with respect to the time period for which the cuff pressure is kept at a constant pressure, it is possible to calculate the respiratory variation on the waveform of artery during the multiple respiratory periods, so that it is possible to obtain the more correct measurement result. Also, the cuff pressure is kept at the constant pressure within a range close to the diastolic blood pressure and not including the pulse wave components of the vein. Therefore, when obtaining the respiratory variation on the waveform of artery, the pulse of the vein little influences, so that it is possible to correctly extract the respiratory variation on the waveform of artery.

In the meantime, some subjects being tested may have the low diastolic blood pressure. Therefore, when obtaining the respiratory variation on the waveform of artery, the pulse wave components of the vein may overlap with the pulse wave components of the artery and may influence the same. Regarding this, according to the illustrative embodiment, the correlation coefficients R1 between the extracted pulse wave components b1, b2, b3, and the representative pulse wave component a1, which is the typical pulse wave of the artery, are calculated and the pulse wave component having low correlativity (a ratio that the pulse wave component of the vein overlaps is high) is excluded to improve the reliability of the respiratory variation on the waveform of artery. In this case, the pulse wave component having low correlativity is excluded based on the correlation coefficients R1 between the extracted pulse wave components b1, b2, b3, . . . obtained by one-time blood pressure measurement and the representative pulse wave component a1. Therefore, it is possible to obtain the respiratory variation on the waveform of artery by using the pulse wave components having higher relativity, as compared to a configuration where the respective blood pressures and the respiratory variation on the waveform of artery are obtained by measurements of separate measuring processes or by mounting the cuff 2 to separate regions, for example. Thereby, it is possible to obtain the respiratory variation on the waveform of artery having high reliability, so that it is possible to assess the correct hemodynamics.

Also, since the mean venous pressure is obtained during the depressurization process of the cuff pressure, it is possible to observe the pulse wave components of the vein while gradually decreasing the pulse wave components of the arterial pressure. For this reason, it is possible to easily detect an amplitude variation in the pulse wave components of the vein, so that it is possible to correctly obtain the mean venous pressure. Also, since the cuff pressure is stepwise decreased, the electromagnetic valve less influences, as compared to a configuration where the cuff pressure is continuously decreased, so that it is possible to more correctly obtain the mean venous pressure.

In the meantime, for some subjects being tested having the low diastolic blood pressure, even though the cuff pressure is reduced, the pulse wave components of the artery may remain without being all eliminated and thus influence the mean venous pressure. Therefore, according to the illustrative embodiment, the correlation coefficients R2 between the extracted pulse wave components c1, c2, c3, . . . and the representative pulse wave component a1, which is a typical pulse wave of the artery, are calculated and the pulse wave component having high correlativity to ratio that the pulse wave component of the artery overlaps is high) is excluded based on the correlation coefficients R2. In this case, the pulse wave component having high correlativity is excluded based on the correlation coefficients R2 between the pulse wave components c1, c2, c3, obtained by one-time blood pressure measurement and the representative pulse wave component a1. Therefore, it is possible to obtain the mean venous pressure by using the pulse wave components having higher relativity, as compared to a configuration where the respective blood pressures and the mean venous pressure are obtained by measurements of separate measuring processes or by mounting the cuff 2 to separate regions and the pulse wave component having high correlativity is excluded based on the correlation coefficients R2 of the pulse wave components extracted therefrom, for example.

Thereby, it is possible to obtain the mean venous pressure less influenced by the arterial pressure and having high reliability, so that it is possible to assess the correct hemodynamics.

Also, since the respective parameters can be obtained in the non-invasive manner and the series of measuring processes are completed in a short time such as about 140 seconds, it is possible to considerably reduce the burden of the subject being tested.

Also, since the relativity between the obtained values of the respiratory variation on the waveform of artery and the obtained values of the venous pressure is displayed as the two-dimensional graph on the display unit 8, a medical staff who is monitoring the biological information can comprehensively determine the two parameters of the respiratory variation on the waveform of artery and the venous pressure by seeing the display unit 8, thereby correctly assessing the hemodynamics of the subject being tested. Furthermore, since the threshold lines m, n, which are the criteria for determining the values of the respiratory variation on the waveform of artery and the values of the mean venous pressure, are displayed on the two-dimensional graph, the medical staff who is monitoring the biological information can easily assess the hemodynamics.

In the meantime, the presently disclosed subject matter is not limited to the above illustrative embodiment and can be appropriately modified and improved. In addition, the materials, shapes, sizes, numerical values, forms, the numbers, arrangement places and the like of the respective constitutional elements in the above illustrative embodiment are arbitrary and are not particularly limited inasmuch as the presently disclosed subject matter can be implemented.

For example, when the pulse wave components of the artery overlap with the pulse wave components of the vein at the time that the value of the diastolic blood pressure is low and the mean venous pressure is obtained, the pulse wave components of the artery detected at the time that the respiratory variation on the waveform of artery is obtained are subtracted from the overlapping pulse wave components. Thereby, it is possible to calculate the correct correlation coefficients R2, thereby improving the reliability of the mean venous pressure. Likewise, when the pulse wave components of the vein overlap with the pulse wave components of the artery at the time that the value of the diastolic blood pressure is low and the respiratory variation on the waveform of artery is obtained, the pulse wave components of the artery detected upon the calculation of the mean venous pressure are subtracted after the calculation of the mean venous pressure is completed. Thereby, it is possible to calculate the correct correlation coefficients R2, thereby improving the reliability of the respiratory variation on the waveform of artery.

Also, the reduction of the cuff pressure during the time period C for which the mean venous pressure is obtained is not limited to the stepwise reduction and the cuff pressure may continuously reduced. Further, the cuff pressure may be stepwise or continuously increased to obtain the mean venous pressure during the pressurization process (the second process). Also, when calculating the correlation coefficient R2 of the pulse wave components at the time that the mean venous pressure is obtained, the pulse wave component of the mean blood pressure is used as the representative pulse wave component a1. However, for example, any one of the pulse wave components b1, b2, b3, . . . having the highest correlativity with the representative pulse wave component a may be used as the representative pulse wave component when measuring the respiratory variation on the waveform of artery. In this case, since the pulse wave components b1, b2, b3 are closer upon the measurement of the mean venous pressure in the elapsed measuring time, it is possible to increase the correctness of the correlation coefficient R2.

Also, when measuring the mean venous pressure, a representative pulse may be determined from the pulse wave components of the artery during the process of measuring the respiratory variation on the waveform of artery, a correlativity between the representative pulse and a pulse wave component for obtaining the mean venous pressure may be obtained to determine the pulse wave component for obtaining the mean venous pressure. Further, the sequence of measuring the pulse wave components may not be the order of the arterial pressure, the respiratory variation on the waveform of artery and the mean venous pressure. For example, the pulse wave components may be measured in order of the mean venous pressure, the respiratory variation on the waveform of artery and the arterial pressure. Also, only the respiratory variation on the waveform of artery and mean venous pressure may be measured.

What is claimed is:

1. A blood pressure measuring apparatus comprising:
a cuff that is mountable to a region of a living body in which a vein and an artery exist, a pressure control unit that controls an applied pressure applied to the region by the cuff mounted to the region;
a detection unit that detects pressure waveforms in which pulse wave components from the region overlap with the applied pressure, the pulse wave components comprise at least one from among pulse wave components of the artery and pulse wave components of the vein;
an analysis unit configured to obtain:
(i) an arterial pressure, a respiratory variation on a waveform of the artery, and a venous pressure, based on the pressure waveforms detected by the detection unit through onetime blood pressure measurement,
(ii) the arterial pressure including at least a diastolic blood pressure and a systolic blood pressure based on data of a third pressure waveform of the pressure waveforms in a third process in which the applied pressure is increased by the pressure control unit from a first time point to a second time point at which the obtaining of the systolic blood pressure is completed,
(iii) the respiratory variation on the waveform of the artery based on data of a first pressure waveform of the pressure waveforms in a first process, in which the applied pressure is reduced from a value at which the obtaining of the systolic blood pressure is completed at the second time point to a value equal to or lower than the diastolic blood pressure and is kept constant by the pressure control unit until a first predetermined time period elapses at a third time point, and
(iv) the venous pressure based on (a) data of a second pressure waveform of the pressure waveforms in a second process in which the applied pressure is decreased by the pressure control unit from the third time point until a second predetermined time period measured from the first time point elapses and (b) either the data of the third pressure waveform in the third process or the data of the first pressure waveform in the first process, the second predetermined time period corresponding to a term of obtaining the arterial pressure, the respiratory variation, and the venous pressure within 140 seconds; and a determination unit configured to:
determine that the first predetermined time period measured from the second time point has elapsed; and
cause the pressure control unit to decrease or increase the applied pressure in the second process based on the determining that the first predetermined time period has elapsed.

2. The blood pressure measuring apparatus according to claim 1, wherein the applied pressure in the first process is within a range which does not include the pulse wave components of the vein.

3. The blood pressure measuring apparatus according to claim 1, further comprising:
a display unit; and
a display control unit that controls the display unit,
wherein the display control unit is configured to display a value of the obtained respiratory variation on the waveform of the artery and a value of the obtained venous pressure with a two-dimensional graph on the display unit.

4. The blood pressure measuring apparatus according to claim 3, wherein a determination criterion for determining the displayed value of the respiratory variation on the waveform of the artery and the displayed value of the venous pressure is displayed on the two-dimensional graph.

5. A blood pressure measuring method for controlling an applied pressure applied to a region of a living body in which a vein and an artery exist by a cuff mountable to the region, the blood pressure measuring method comprising:
detecting pressure waveforms in which pulse wave components are overlapped with the applied pressure; and
obtaining an arterial pressure, a respiratory variation on a waveform of the artery, and a venous pressure, based on the pressure waveforms detected through onetime blood pressure measurement, wherein
the obtaining the arterial pressure includes obtaining at least a diastolic blood pressure and a systolic blood pressure based on data of a third pressure waveform of the pressure waveforms in a third process in which the applied pressure is increased from a first time point to a second time point at which the obtaining of the systolic blood pressure is completed,
the obtaining the respiratory variation on the waveform of the artery is based on data of a first pressure waveform of the pressure waveforms in a first process, in which the applied pressure is reduced from a value at which the obtaining of the systolic blood pressure is completed at the second time point to a value equal to or lower than the diastolic blood pressure and is kept constant until a first predetermined time period elapses at a third time point,
the obtaining the venous pressure includes (i) determining that the first predetermined time period measured from the second time point elapsed, (ii) causing the applied pressure to decrease based on the determining that the first predetermined time period elapsed, and (iii) obtaining the venous pressure based on (a) data of a second pressure waveform of the pressure waveforms in a second process in which the applied pressure is decreased from the third time point until a second predetermined time period measured from the first time point elapses and (b) either the data of the third pressure waveform in the third process or the data of the first pressure waveform in the first process, and
the second predetermined time period is a term of obtaining the respiratory variation, the venous pressure, and the arterial pressure that is within 140 seconds.

6. The blood pressure measuring apparatus according to claim 1, wherein the term of obtaining the respiratory variation is within 60 seconds.

7. The blood pressure measuring apparatus according to claim 1, wherein an interval of decreasing the applied pressure when obtaining the venous pressure is at least 6 seconds.

8. The blood pressure measuring apparatus according to claim 1, wherein the term of obtaining the arterial pressure is within 15 seconds.

9. The blood pressure measuring apparatus according to claim 1, wherein the term of obtaining the respiratory variation is within 60 seconds,
an interval of decreasing the applied pressure when obtaining the venous pressure is within 6 seconds, and
the term of obtaining the arterial pressure is within 15 seconds.

10. A blood pressure measuring apparatus comprising:
a cuff that is mountable to a region of a living body in which a vein and an artery exist;
a pressure control unit that controls an applied pressure applied to the region by the cuff mounted to the region;
a detection unit that detects pressure waveforms in which pulse wave components from the region overlap with the applied pressure;
an analysis unit configured to obtain:
(i) an arterial pressure, a respiratory variation on a waveform of the artery, and a venous pressure, based on the pressure waveforms detected by the detection unit through onetime blood pressure measurement,
(ii) the respiratory variation on the waveform of the artery based on data of a first pressure waveform of the pressure waveforms in a first process, in which the applied pressure is kept at a constant pressure by the pressure control unit,
(iii) the venous pressure based on (a) data of a second pressure waveform of the pressure waveforms in a second process in which the applied pressure is decreased or increased by the pressure control unit and (b) either the data of a third pressure waveform in a third process or the data of the first pressure waveform in the first process, and
(iv) the arterial pressure based on data of the third pressure waveform of the pressure waveforms in the third process in which the applied pressure is decreased or increased by the pressure control unit,
wherein each of the respiratory variation, the venous pressure, and the arterial pressure is obtained for a corresponding obtaining term,
wherein the blood pressure measuring apparatus further comprises a determination unit configured to (i) determine that a first predetermined time period measured from a start of a measurement of the respiratory variation on the waveform of artery has elapsed, and (ii) cause the pressure control unit to decrease or increase the applied pressure in the second process based on the determining that the first predetermined time period has elapsed, and
wherein the analysis unit is configured to obtain the venous pressure using only the cuff.

11. The blood pressure measuring apparatus according to claim 1, wherein the analysis unit is configured to obtain the venous pressure using only the cuff.

12. The blood pressure measuring method according to claim 5, wherein the obtaining the venous pressure further comprises obtaining the venous pressure using only the cuff.

* * * * *